US008304534B2

(12) United States Patent
Nagura et al.

(10) Patent No.: US 8,304,534 B2
(45) Date of Patent: Nov. 6, 2012

(54) PROCESS FOR PRODUCING DIFRUCTOSE DIANHYDRIDE III CRYSTALS

(75) Inventors: Taizo Nagura, Obihiro (JP); Katsuya Honjyo, Obihiro (JP); Hiroto Kikuchi, Obihiro (JP); Norimitsu Takagi, Obihiro (JP); Tsutomu Aritsuka, Obihiro (JP)

(73) Assignee: Nippon Beet Sugar Manufacturing Co., Ltd., Tokyo (JP)

( * ) Notice: Subject to any disclaimer, the term of this patent is extended or adjusted under 35 U.S.C. 154(b) by 0 days.

(21) Appl. No.: 13/210,595

(22) Filed: Aug. 16, 2011

(65) Prior Publication Data

US 2011/0300581 A1    Dec. 8, 2011

Related U.S. Application Data

(63) Continuation of application No. 11/722,936, filed as application No. PCT/JP2004/019832 on Dec. 28, 2004, now Pat. No. 8,039,615.

(51) Int. Cl.
| | |
|---|---|
| *C07H 1/00* | (2006.01) |
| *C07H 3/00* | (2006.01) |
| *C07H 3/02* | (2006.01) |
| *C08B 37/00* | (2006.01) |
| *C13K 5/00* | (2006.01) |
| *C13K 7/00* | (2006.01) |

(52) U.S. Cl. .................... 536/125; 536/123.13; 536/126
(58) Field of Classification Search ........................ None
See application file for complete search history.

(56) References Cited

U.S. PATENT DOCUMENTS

2006/0051845 A1    3/2006    Kikuchi et al.

FOREIGN PATENT DOCUMENTS

| JP | 117688 | 11/1974 |
|---|---|---|
| JP | 56-26400 | 6/1981 |
| JP | 1-285195 | 11/1989 |
| JP | 2-115196 | 4/1990 |
| JP | 3-259090 | 11/1991 |
| JP | 4-271792 | 9/1992 |
| JP | 05-168419 | 7/1993 |
| JP | 11-43438 | 2/1999 |
| JP | 11-103814 | 4/1999 |
| JP | 2002-17391 | 1/2002 |
| JP | 2003-026610 | 1/2003 |
| JP | 2004-305125 | 11/2004 |
| WO | WO2004-078989 | 9/2004 |

OTHER PUBLICATIONS

J. Ferment.Technol., vol. 52, No. 3 p. 164-170 1974 "Preparation of Di-d-fructofuranose 1,2':2,3' dianhydride by the Cultivation of Arthrobacter ureafaciens in the Inulin-containing Synthetic and Vegetable Media" Elichi Shirasawa et al.
Landbauforschung Voelkenrode., 3(51): 131-136 (vol. 518, No. 3, pp. 131 to 136, 2001); "Effective development of a Biotechnical process: Screening, genetic engineering, and immobilization for the enzymatic conversion of insulin to DFA IIIon industrial scale" Ulrich Jahnz et al.
Journal of Fermentation and Bioengineering, vol. 72, No. 4, 258-261, 1991, "Production of Inulin Fructotransferase (Depolymerizing) by *Arthrobacter* sp. H65-7 and Preparation of DFA III from Inulin by the Enzyme", Atsushi Yokota et al.
Atsushi Yokota, et al., "Purification and Properties of an Inulin Fructotransferase (Depolymerizing) from *Arthrobacter* sp. H65-7", Journal of Fermentation and Bioengineering, vol. 72, No. 4, 1991, pp. 262-265.
Hiroto Kikuchi, et al., Journal of Agriculture and Horticulture, vol. 75, No. 9, 2000, pp. 9-14 (with English translation).
Hiroto Kikuchi, et al., "Physical, Chemical and Physiological Properties of Difructose Anhydride III Produced from Inulin by Enzymatic Reaction", Journal of Applied Glycoscience, vol. 51, No. 4, 2004, pp. 291-296.
Reduced Edition (1) of "encyclopedia of chemistry"), Kyoritsu Shuppan Co., Ltd., Feb. 15, 1987, p. 678 (w/Certified English Partial Translation).
Base of Sugar Chemistry, Kodansha Ltd., Aug. 10, 1995, p. 39 (w/Certified English Partial Translation).
International Search Report in PCT/JP2004/019832 dated Mar. 15, 2005.
Notice of Reasons for Refusal in Japanese Application No. 2006-550548, dated Jan. 10, 2012. (w/English Translation).
Experimental lecture of biochemistry No. 4, Chemistry of carbohydrate, vol. 1, Tokyo Kagaku Dojin Co., Ltd., Apr. 12, 1976. (w/English Translation).

*Primary Examiner* — Layla Bland
(74) *Attorney, Agent, or Firm* — Oblon, Spivak, McClelland, Maier & Neustadt, L.L.P.

(57) ABSTRACT

A process for producing the crystals of difructose dianhydride III (DFA III), namely a indigestible disaccharide where two fructose molecules are bonded to each other at positions 1, 2' and 2,3' (di-D-fructofuranose-1,2':2,3'-dianhydride), where solutions containing DFA III are adjusted to and/or maintained at pH 5 or more, preferably pH 5 to 8, and more preferably 6 to 8. DFA III can be produced industrially without lowering the crystal yield even when the crystallization thereof is done in a recycling system; additionally by adjusting the total fructose content in mother solutions for (crude) crystallization to 5% or less per a solid content basis and adjusting the fructose content to 1% or less, DFA III can more effectively be produced.

13 Claims, 8 Drawing Sheets

TEST PERIOD (DAYS)

TEST PERIOD (DAYS)

US 8,304,534 B2

PROCESS FOR PRODUCING DIFRUCTOSE DIANHYDRIDE III CRYSTALS

This application is a Continuation of National Stage Application PCT/JP04/19832 filed on Dec. 28, 2004.

TECHNICAL FIELD

The present invention relates to a process for efficiently producing the crystals of difructose dianhydride III (sometimes referred to as DFA III hereinafter). In a recycling system for producing DFA III, in accordance with the invention, the crystal yield is never lowered. Therefore, the process of the invention is very excellent as an industrial process for producing DFA III.

BACKGROUND OF THE INVENTION

DFA III is a functional oligosaccharide with an effect on promoting the absorption of minerals primarily including calcium, a diuretic effect, and an effect of ameliorating constipation. DFA III is a cyclic disaccharide (di-D-fructofuranose-2',1:2,3'-dianhydride), where the reducing end of each of two fructose molecules is bonded to a hydroxyl group at a position other than the reducing end of the other fructose molecule. DFA III is highly soluble in water at a solubility of 90 to 95% of the water solubility of sucrose, while the sweetness level is about 52% of that of sucrose. Additionally, DFA III is a substance highly resistant against heat and acids.

As one process for producing DFA III, a process for producing DFA III has been proposed, comprising interacting a bacterium of the species *Arthrobacter ureafaciens* or an enzyme generated by the species with inulin and/or an inulin-containing plant extract to prepare a solution containing DFA III, passing the solution containing DFA III through a column packed with active charcoal to allow DFA III to be adsorbed on the active charcoal, subsequently eluting the column with ethanol to recover a fraction at a high DFA III content and evaporating and drying the fraction (see for example Patent Reference 1).

Another process for producing DFA III has also been proposed, comprising passing inulin and/or an inulin-containing plant extract through a column packed with inulin fructotransferase immobilized on an immobilizing material, to generate a DFA III-containing solution, and subjecting the DFA III-containing solution to a purification step for example with anion exchange resin or active charcoal to generate a DFA III-containing syrup or an evaporated and dried product (see for example Patent Reference 2).

Furthermore, it is also described that the reaction of inulin with inulase II allows for the industrial production of DFA III at a high purity (see for example Patent Reference 3).

However, absolutely not any of these references tells about the yield of crystallized DFA III. Not any report has been issued about an efficient industrial production of the crystals of DFA III. Therefore, such production has been totally unknown.

Patent Reference 1
  JP-B-56-26400
Patent Reference 2
  JP-A-1-285195
Patent Reference 3
  JP-A-11-43438

Problems that the Invention is to Solve

Following the recent development of a useful application of DFA III, demands toward DFA III have been increasing. For medical use as well as for dietary use, the crystals of DFA III at a high purity have been desired, from which sugars except DFA III and other various impurities are removed. Desirably, a process for more efficiently producing the crystals of DFA III from solutions containing DFA III and an industrial process for producing crystallized DFA III, in particular, may be established.

Means for Solving the Problems

In such technical circumstances, the invention has been achieved for the purpose of developing a process for producing the crystals of DFA III, particularly an industrial process for efficiently producing the crystals of DFA III.

Thus, the inventors developed a process for producing the crystals of IDEA III as a product, comprising defecating and filtering a DFA III-containing solution, subsequently concentrating the resulting filtrate for crude crystallization to separate a crude crystal syrup, dissolving the crude crystals thus and defecating and filtering the resulting solution, concentrating the filtrate, crystallizing the concentrate, and separating the crystal syrup. For efficient preparation and industrialization, furthermore, the inventors constituted a recycling system for recycling the crude crystal syrup and/or the crystal syrup separated as described above to a crystallization step to continuously produce the crystals of DFA III. The inventors first encountered a serious drawback such that the crystal yield of DFA III was decreased over time, involving difficulty in producing any crystals of DFA III, so that the industrial production thereof was substantially never achieved.

So as to overcome the serious drawback first found, the inventors thoroughly investigated the cause of the decrease of the crystal yield of DFA III from various aspects.

DFA III-containing solutions contain substances other than DFA III. These may be for example substances derived from chicory in extracting inulin from plants such as chicory, or substances synthesized in generating inulin from sugar via enzymatic synthetic preparation, or enzymatically degraded inulin-derived substances via the enzymatic reaction for producing DFA III from inulin. In the process for producing the crystals of DFA III, DFA III-containing solutions are retained for such a long time and the solutions are exposed to such severe conditions including high temperature during the concentration process of the solutions for a long time that the composition of the DFA III-containing solutions may be modified under these conditions, to generate new other substances. Various substances as described above may affect the crystallization of IDEA III. Because the DFA III-containing solutions are recycled at the purification and crystallization step of DFA III, new substances other than DFA III generated as described above may sometimes accumulate.

Inulin as one of raw materials for DFA III is a polysaccharide where numerous fructose molecules are connected in series to one glucose molecule. When an enzyme with hydrolysis and transition activities reacts with inulin, DFA III is generated as the main component while as other by-products, fructooligosaccharides such as tetrasaccharide (G-F-F-F) and pentasaccharide (G-F-F-F-F) are generated. These tetrasaccharide and pentasaccharide are poorly resistant against heat and are therefore modified at a step at high temperature as in the concentration step, to be decomposed into sugars of smaller molecular weights, finally into organic acids and the like. Consequently, the DFA III-containing solutions are at a decreased pH. The inventors found that the decomposition thereof was further accelerated at the defecation and crystallization steps of DFA III especially in the production process in a recycling system.

At the enzymatic reaction step of generating DFA III from inulin, the reaction proceeds under relatively mild temperature conditions such as around 60° C. Although the initial enzymatic reaction was at a neutral pH range (pH 6-7), the reaction solution on the completion of the reaction was decreased to pH 4 or therearound. Thus, it was found that the DFA III solutions enzymatically synthesized by the enzymatic reaction process are generally at pH 5 or less and it became one of the factors to cause the decomposition of tetrasaccharides and pentasaccharides, at a subsequent step leading to the DFA III crystallization.

In progress to a crystallization step of DFA III, substances other than DFA III are mostly derived from sugars, where monosaccharides glucose and fructose, a disaccharide sucrose, trisaccharides, tetrasaccharides and substances larger than (fructooligosaccharides), organic acids and the like may exist in mixture. Additionally, DFA III is a substance hardly decomposed thermally or with acids, as described above.

In view of those described above, the inventors made investigations from various aspects about diverse substances in DFA III-containing solutions with an influence on producing the crystals of DFA III. Surprisingly, the inventors first found consequently that the pH of a solution containing DFA III and sugars existing in admixture, particularly fructose and sucrose, affected specifically the crystallization of DFA III.

The inventors therefore made investigations about factors specifically affecting the crystallization of DFA III from various aspects, which factors were first found by the inventors.

With attention focused on the substances except DFA III, the inventors made various investigations. Consequently, the inventors found that the decomposition of substances readily decomposable at a series of steps for crystallizing DFA III could be suppressed and the conversion of such substances into other substances could be blocked at minimum, by maintaining and/or adjusting all of the solutions containing DFA III at the defecation, concentration and crystallization steps of DFA III to pH 5 or more, preferably to pH 5 to 8, more preferably to pH 6 to 8 (by the glass electrode method). Additionally, the inventors newly found that by crystallizing DFA III from a mother solution for the (crude) crystallization at pH 5 or more, preferably pH 6 to 8, the crystal yield was never lowered but was maintained or increased.

It has never been known that the crystal yields of sugars such as DFA III and other sugars are modified by the pH of mother solutions for the crystallization. Thus, the finding is a totally new finding.

As a method for maintaining and adjusting the pH of such solutions at the individual steps in producing DFA III within the range described above, the solutions at the individual steps should effectively be controlled at 70° C. or less as much as possible. Additionally, an alkaline agent may be added to actively adjust the pH. The alkaline agent to be used includes for example sodium hydroxide (caustic soda), potassium hydroxide (caustic potassium) and sodium carbonate (lime soda). Additionally, the purity of DFA III in the solutions at the steps can be increased and the pH decrease can be prevented, concurrently, by simultaneously removing acidic substance such as organic acids and sugars except DFA III in the solutions at the steps by using a chromatographic method.

As a method other than the method described above, a DFA III-containing solution containing also acidic substances is passed through anion exchange resins to adsorb the acidic substances via ion exchange to remove the acidic substances.

The inventors newly found that fructose and sucrose contained in a mother solution containing DFA III for the crystallization were factors causing the inhibition of the crystallization of DFA III. It was found that the fructose content at 5% or less, preferably 1% or less on a solid content basis in a mother solution for the crystallization enhanced the crystal yield of DFA III during the crystallization thereof.

Under the condition that the pH value of a mother solution for crystallization of DFA III was 5 to 7 and the supersaturation degree (referred to as supersaturation degree "S" in accordance with the invention) of DFA III concentration in the mother solution to the solubility of DFA III at a temperature on the completion of the crystallization was 4.4 or more, the flowability of the massecuite was so significantly reduced in the mother solution containing DFA III at any purity for the crystallization, so that it was found that the purging involved was much difficulty. Under a condition that the supersaturation degree "S" was 4.1 or less, alternatively, the massecuite had such suitable flowability that the purging could be done without any difficulty. Thus, it was found that the supersaturation degree "S" on the basis of the temperature on the completion of the crystallization was 4.1 or less under a condition for the industrial crystal production of DFA III from a mother solution for the crystallization at pH 5 or more. When the supersaturation degree "S" was less than 1.3, the crystal yield was 20% or less. Accordingly, it was found that the supersaturation degree "S" was preferably 1.3 or more to 4.1 or less, more preferably 1.5 or more to 4.1 or less and still more preferably 2.3 or more to 4.1 or less, from the standpoint of the crystal yield.

The term "solid concentration" referred to in accordance with the invention is the ratio of solid in a solution (in w/w %), as determined on the basis of the weight of the solid remaining after water in the solution is removed by drying method. For the practical control of the production process, the value of R-Bx (Refractometric Brix Degree) can also be used in a simple manner.

Based on these useful new findings, the invention has been achieved finally, as a consequence of further research works and examinations.

Figure 1:
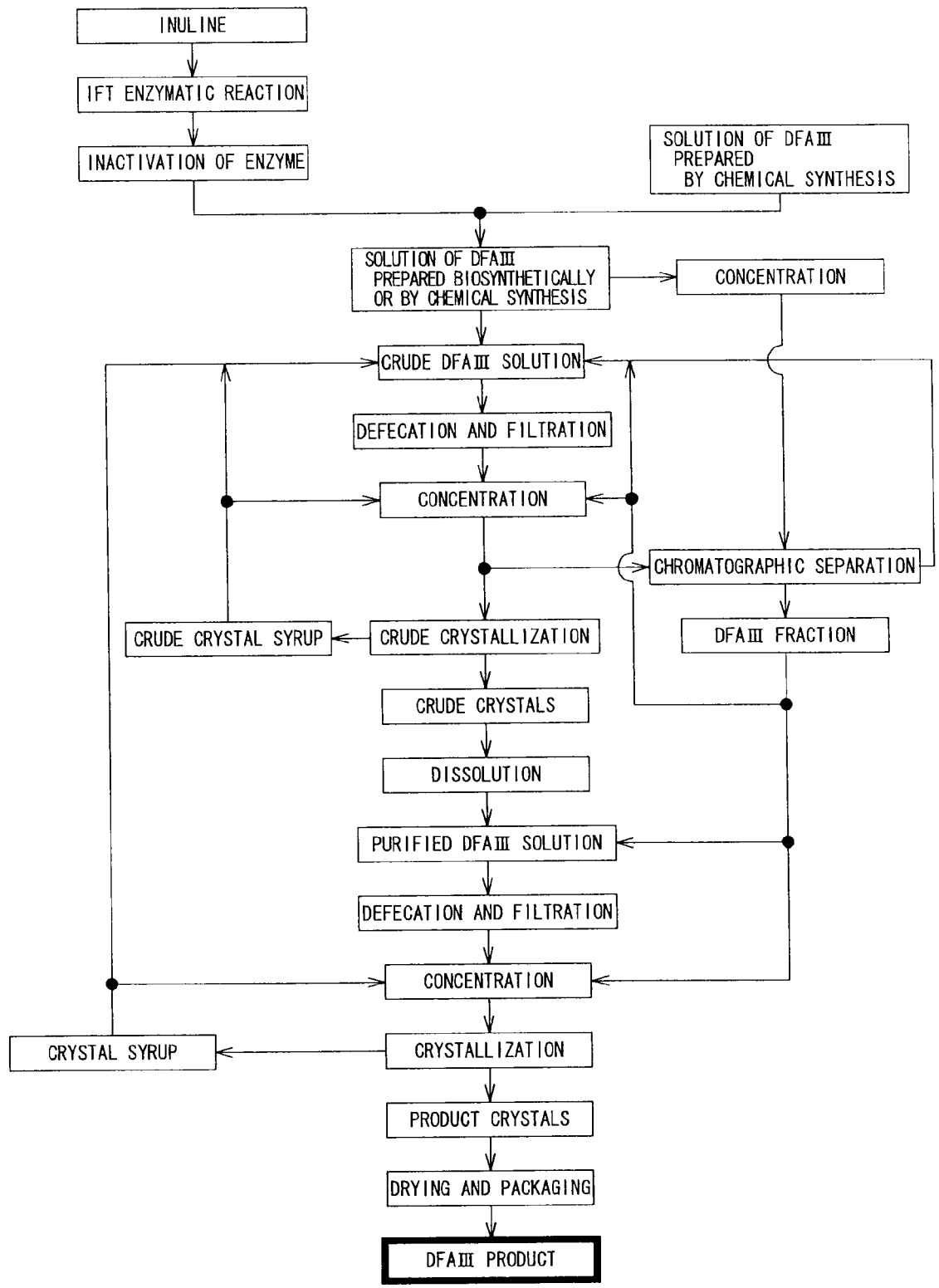
FIG. 1 shows an example of a flow chart of the production of the crystals of DFA III, comprising the purification and crystallization step of a solution containing DFA III.

The invention is now described in detail hereinbelow.

The invention relates to an efficient industrial production of the crystals of DFA III at a high purity without lowering the crystal yield, by purifying a liquid containing DFA III. With attention focused on the significance of the pH of the liquid containing DFA III, first, the inventors made investigations to find that the liquid should essentially be adjusted to pH 5 or more. Based on the useful new finding, the inventors made research works and examinations. Finally, the invention has been achieved.

In accordance with the invention, a liquid containing DFA III is purified to produce the crystals of DFA III, where the liquid containing DFA III is at pH 5 or more.

Industrial crystallization of DFA III has never been done in the related art. Therefore, no examination has been done about the pH thereof or no attention has been focused on the pH thereof. The pH influence on the DFA III crystallization was first focused on by the present inventors during the course of research works about the industrial DFA III crystallization as made by the inventors. Thus, it is an absolutely new finding. In accordance with the invention, the problematic issue has drawn attention for the first time during the industrial research works relating to the DFA III crystallization. Thus, it can be recognized that the technical issue itself is new. Hence, reasonably, the means for solving the problem is also novel. The invention encompasses those described below.

1. A process for producing the crystals of difructose dianhydride III (DFA III), where a solution containing difructose dianhydride III (DFA III) is at pH 5 or more.

2. A process for producing the crystals of DFA III as described above in 1, where the pH of the solution containing DFA III is adjusted and maintained with at least one of an alkali addition method, a chromatographic method and an anion exchange resin method.

3. A process for producing the crystals of DFA III as described above in 1 and 2, where the solution containing DFA III is a solution prepared by reacting inulin with fructosyltransferase, and defecating and filtering the resulting solution.

4. A process for producing the crystals of DFA III as described above in 3, where inulin is at a fructose polymerization degree of 10 to 60 and at a polysaccharide purity of 70% or more in dry substance.

5. A process for producing the crystals of DFA III as described above in any one of 1 through 4, comprising a step of defecating and filtering solutions containing DFA III and concentrating the resulting filtrates for crystallization (purification and crystallization step), which step ranges from crude DFA III solutions through crude crystallization to crystallization as a product, where at least one of the solutions containing DFA III is at pH 5 or more.

6. A process for producing the crystals of DFA III as described above in 5, where the purification and crystallization step is done in a recycling system.

7. A process for producing the crystals of DFA III as described above in any one of 1 through 6, where the supersaturation degree of a mother solution for the crystallization or a mother solution for the crude crystallization, which is on the basis of the solubility at the temperature on the completion of the cooling and crystallization, is 1.3 to 4.1.

8. A process for producing the crystals of DFA III, where the fructose content in dry substance in a DFA III-containing mother solution for the crystallization or a DFA III-containing mother solution for the crude crystallization is 5% or less.

9. A process for producing the crystals of DFA III as described above in 8, where fructooligosaccharide and/or fructose is removed by using any one of chromatographic treatment and yeast treatment as a method for adjusting the fructose content in dry substance to 5% or less.

10. The crystals of DFA III as produced by a process described above in any one of 1 through 9.

In accordance with the invention, the crystals of DFA III at a high purity can efficiently be produced industrially by purifying solutions containing DFA III, where at least one, preferably all of the solutions containing DFA III are at pH or more.

So as to practice the invention, at least one or all of the solutions containing DFA III are adjusted to pH 5 or more for crystallization during the production steps of the crystals of DFA III (one example thereof is shown in FIG. 1).

The process for producing the crystals of DFA III is described below with reference to FIG. 1 illustrating one example thereof.

Raw materials for solutions containing DFA III include solutions of DFA III synthetically prepared by reacting inulin or an inulin-containing solution with fructosyltransferase, and additionally include solutions of DFA III prepared by chemical synthesis.

Inulin as one of the raw materials is a fructose polymer where numerous fructose molecules are connected in series to one glucose molecule. Enzymes working for generating DFA III broadly including fructosyltransferase, preferably inulin fructotransferase (IFT) react with the raw material inulin.

Microorganisms generating IFT include those described below.

Non-limiting examples thereof are listed below.

*Arthrobacter* sp.; *Arthrobacter ureafaciens* IFO 12140; *Arthrobacter globiformis* IFO 12137; *Arthrobacter pascens* IFO 12139; *Bacillus* sp.; *Kluyveromyces marxianus* var. marxianus: *Streptomyces* sp.; *Enterobacter* sp.

In case of using enzymes derived from these microorganisms, then, separated and purified enzymes and crudely purified enzymes, microbial cultures, and treated products of microbial cultures (culture supernatants, separated bacterial cells, disrupted bacterial cells, etc.) may also be used. In case that the crystal of DFA III is to be used for foods, fructosyltransferase, particularly IFT is preferably used as such enzyme. In addition to the enzymes derived from these microorganisms, *Arthrobacter* sp. strain AHU 1753 internationally deposited lately as FERN BP-8296 at the International Patent Organism Depositary, the National Institute of Advanced Industrial Science and Technology has a great potency to generate IFT. Therefore, the enzyme derived from the strain can be used preferably.

For example, reaction with a crude enzyme, a purified enzyme, or an enzyme-containing material of inulin fructotransferase (depolymerizing) (IFT) derived from above-mentioned *Arthrobacter* sp. strain AHU 1753 (FERM BP-8296) at 5000 units of the enzyme/kgφinulin under agitation at 60° C. for 24 hours allows hydration and transfer to generate an enzymatic reaction solution containing DFA III. By inactivating the enzyme, a solution of DFA III prepared enzymatically can be obtained. A solution of DFA III prepared by chemical synthesis can be also obtained.

The thus obtained solution of DFA III prepared enzymatically or by chemical synthesis is defined, singly or in admixture with other solutions containing DFA III, as a crude DFA III solution. The crude DFA III solution is subsequently defecated and filtered. The defecation and filtration step means a step for the treatment of the crude DFA III solution with active charcoal and the treatment for separating solids from liquids. The treatment with active charcoal is a treatment comprising adding a small amount of powdery active charcoal to the crude DFA III solution to adsorb impurities except DFA III onto the active charcoal, and if necessary to heat and/or agitate the resulting mixture.

As the powdery active charcoal, a powdery active charcoal of a mean particle size of 15 to 50 microns, preferably 25 to 45 microns, more preferably about 35 microns is used, which is at the maximum particle size of 200 microns or less, preferably 170 microns or less, more preferably 150 microns or less, for example 147 microns or less. The amount of the powdery active charcoal to be added is 5% or less, preferably 0.1 to 3%, more preferably 0.5 to 1.5% of the solid contents, and may be adjusted appropriately, depending on the composition of the crude DFA III solution.

For the treatment for separating solids from liquids, at least one of filtration with auxiliary filtration agents such as Hi-Flo Supercell (Wako Pure Chemical Ind.) and diatomaceous earth (for example, filtration with a ceramic filtration machine; Type PR-12 manufactured by Japan Pall K.K. may be used), filtration with a membrane filter (MF), the continuous centrifugation method, the molecular sieve method, the reverse osmosis method, and, in some cases, an ultrafiltration (UF) membrane are appropriately used. The separation of solids from liquids may be done at atmospheric pressure, under pressure or at reduced pressure.

Specifically, for example, Taiko Active Charcoal S (manufactured by Futamura Kagaku Kogyo K.K.; the mean particle size of about 35 microns but not more than 147 microns) is added at a ratio of 1% on a solid content basis to the inactivated IFT enzyme solution, for agitation at 60° C. for 10 minutes. On completion, the solution is filtered through diatomaceous earth (Radiolite 700, manufactured by Showa Chemical Ind.). Specifically, the diatomaceous earth is pre-coated on the exterior surface of a ceramic cylinder (ceramic tube of Type PR-12 as manufactured by Japan Pall K.K.), while a reaction solution containing active charcoal is passed through the outside of the cylinder under pressure, and is then filtered under pressure, to recover the filtrate from the inside of the cylinder.

The filtrate recovered via the defecation and filtration treatment of the DFA III-containing solution (crude solution) is concentrated by a general method. For example, the filtrate is concentrated in a calandria evaporator for use in producing sugar and the like (for example, at 60 to 80° C. and at 120 mmHg or less), to obtain a concentrate solution. The concentrate solution may satisfactorily be concentrated to a solid concentration of 60 to 85%, for example about 77%.

In accordance with the invention, the crude DFA III solution obtained from a solution of DFA III prepared enzymatically or a solution of DFA III prepared by chemical synthesis is preferably retained at pH 5 or more between the defecation and filtration step and the concentration step. By adding for example sodium hydroxide to the crude solution, the crude solution may be adjusted to pH 5 or more.

A mother solution as the concentrate solution thus obtained, namely a mother solution for the crude crystallization (at about 60° C.) is transferred into a crystallizer, to generate the crystals of DFA III in a cooling mode or a boiling system to obtain the crude crystals. In this case, the crystal of DFA III ground in a mortar and the like is dispersed in alcohol and the like, which is defined as a seed. The seed (seed crystals) is added at an appropriate amount to the mother solution in appropriate timing to grow the crystals. The seeding method includes full seeding method and shock seeding method. According to the full seeding method, the amount of the seed is adjusted to 1% or more of the amount of DFA III in a mother solution for the crystallization or a mother solution for the crude crystallization, to make a shift of the particle distribution of the crystals of DFA III toward a smaller size. By the cooling crystallization method, the crystals of DFA III particles are smaller at a lower seeding temperature by both the seeding methods. The temperature gradient during cooling and crystallization is adjusted initially to a smaller level and subsequently to a larger level, which makes a smaller variation of the crystal particle size. As the crystallizer, a crystallizer equipped with a circulating system and/or an agitation system is preferably used.

The mother solution for the crude crystallization so as to deposit the crystals is separated with a centrifuge (3000 rpm, 1200 G) into a crude crystals of DFA III and a crude crystal syrup.

The crude crystals of DFA III are again dissolved in lukewarm water, to prepare a purified DFA III solution, which is passed through a defecation and filtration step, then concentrated and crystallized by the same method for the crude crystal, to obtain the product crystals. The resulting crystals are an octahedron odorless, colorless and transparent in a neutral region, of which the melting point is 163.7° C. and the optical rotation $[\alpha]_D$ is 134.5.

In case that the pH of the solutions at the individual steps is adjusted and retained at 5 or more in accordance with the invention, the crude crystal syrup and/or the crystal syrup separated in the aforementioned flow may be recycled to the crystal production system, if necessary. Using such recycling system, further, the recovery ratio of DFA III can be improved. When a recycling system is established where the pH of the solutions from the individual steps is never maintained or adjusted, substances inhibiting the crystallization of DFA III, such as monosaccharide (fructose, in particular) and sucrose, significantly increase and accumulate in the solutions at the steps, while the pH of the mother solutions for the crystallization is greatly lowered, leading to the decrease of the crystal yield during the DFA crystallization step and additionally falling into a state such as no achievement of the crystallization, most undesirably.

Figure 2:
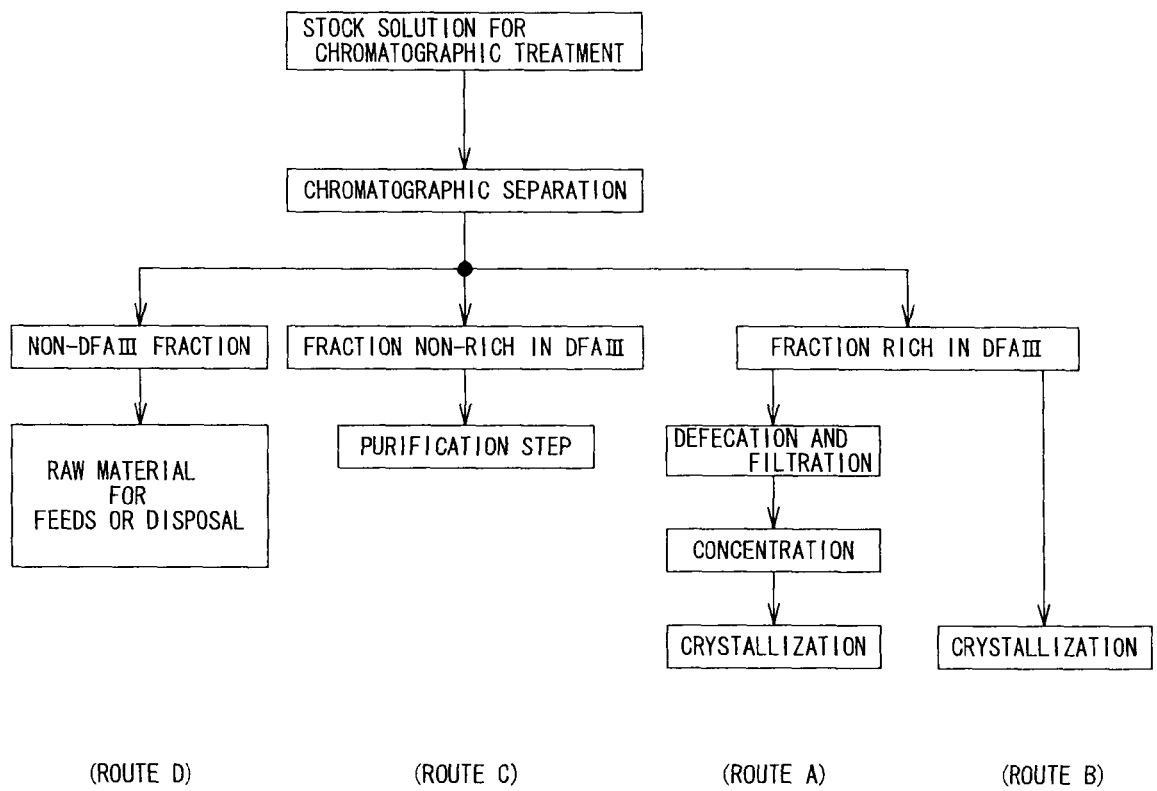
FIG. 2 shows an example of a flow chart of the purification by chromatography.

In accordance with the invention, it was found that the solutions from the individual steps were maintained or adjusted to pH 5 or more to suppress the generation of monosaccharides, sucrose or acidic substances (such as organic acids) as factors inhibiting the crystallization of DFA III. In addition to the method comprising adding alkaline agents, the chromatographic separation method and the yeast treatment of the solutions containing the inhibitory substances from the steps enable the removal of the inhibitory substances and the purification and crystallization of DFA III. In other words, various products generated during all the steps for the purification and crystallization of DFA III (FIG. 1) were used in stock solutions for chromatography (at 40 to 75% of the solid concentration), to allow the purification and crystallization for solutions containing DFA III. One example of the purification flow chart by the chromatographic treatment is shown in FIG. 2.

The stock solution for chromatography (at a solid concentration of 40 to 75%) is treated by chromatography, to separate a fraction of DFA III. A fraction enriched with DFA III at a purity similar to that of the redissolved solution described above (DFA III solution) is used as a solution for purifying DFA III, for defecation and filtration, or for concentration and crystallization, to produce the product crystals (Route A). Otherwise, the enriched fraction is used as it is for crystallization (Route B). Unlike the fraction enriched with DFA III, a fraction not enriched with DFA III, which is at a low content of DFA III, may satisfactorily be recycled to an appropriate position in the production flow chart (in the whole purification step ranging from the DFA III-containing solutions to the product DFA III, as shown in FIG. 1) (Route C). Further, a fraction not enriched with DFA III, containing fructooligosaccharide, monosaccharides such as fructose and acidic substances but containing only a small amount of DFA III, can be used as a raw material for feeds or may be disposed.

For the chromatographic separation method, the fixed bed mode (one-path mode), the continuous mode (simulated moving bed mode) and the semi-continuous mode (a combination of the fixed bed mode and the continuous mode) may be used. As the ion exchange resins to be packed in such apparatuses, highly acidic ion exchange resins of for example Na form, K form and Ca form for use in chromatography can be used. The resins are for example styrene-divinylbenzene-series resins of a uniform particle size. Various chromatographic resins are commercially available from manufacturers of ion exchange resins. Any such chromatographic resins applicable to sugar solutions may be used satisfactorily. Incase that the purity of DFA III is low in a mother solution for the crystallization, the chromatographic treatment is appropriately used so as to raise the purity.

The yeast treatment may satisfactorily be done by putting the DFA III-containing solution in contact with yeast. Both the solution and yeast may be mixed together and incubated under agitation if necessary or may be cultured in air purging. As the yeast, there may be used appropriately baker's yeast, Japanese sake yeast, beer yeast, wine yeast and other various types of yeast. Additionally, dry yeast, squeezed yeast and other various commercially available yeast products may also be used. Because yeast decomposes or allows the incorporation of fructooligosaccharide, sucrose and monosaccharides into bacterial cells, the yeast treatment is useful mainly for removing fructooligosaccharide, sucrose and/or monosaccharides outside the system.

In accordance with the invention, DFA III-containing solutions (mother solutions for the crystallization) at less than 60% of the purity of DFA III may industrially be crystallized. So as to raise the purification level of the DFA III-containing solutions at less than 60% of the purity of DFA III, in accordance with the invention, the DFA III-containing solutions are treated by at least one of the yeast treatment, the defecation and filtration treatment and the chromatographic treatment, to highly raise the purity of DFA III in the DFA III-containing solutions.

The main terms in accordance with the invention are now described below with reference to the production flow chart of the crystals of DFA III as shown in FIG. 1.

(Inulin)

The term "inulin" means plant-derived- or enzymatically synthesized product-derived inulin or inulin-containing liquids, including for example plant extracts from for example Jerusalem artichoke, burdock or chicory, solutions containing synthetic inulin prepared by the reaction of sucrose with an inulin synthase, or solutions resulting from the defecation and filtration of such solutions, and additionally including inulin-containing powders resulting from drying up the individual solutions or crystallizing DFA III therein.

Using inulin as one of raw materials for solutions containing DFA III, which is at a fructose polymerization degree of 10 to 60 and at a polysaccharide purity of 70% or more, preferably 80% or more on a solid content basis, DFA III is efficiently generated. Using then the DFA III-containing solution, the crystals of DFA III are produced efficiently.

(Solutions of DFA III Prepared Enzymatically or by Chemical Synthesis)

Solutions of DFA III prepared enzymatically or by chemical synthesis include solutions prepared by reacting inulin with the enzyme to generate a solution containing DFA III and inactivating the enzyme if necessary and solutions of DFA III prepared by chemical synthesis.

(Crude DFA III Solution)

The term "crude DFA III solution" means the solutions of DFA III prepared enzymatically or by chemical synthesis themselves, and solutions comprising at least one or more of crude crystal syrup, crystal syrup, chromatographically separated solutions, and fractions of DFA III, as prepared by separating mother solutions into solids and liquids after crystallization at crystallization steps (for crude crystallization, and crystallization). Additionally, the term also means a solution prepared by mixing the solution of DFA III prepared enzymatically or by chemical synthesis with at least one of such crude crystal syrup, crystal syrup, chromatographically separated solutions and fractions of DFA III as obtained by chromatographic separation.

(Mother Solution for Crude Crystallization)

The term "mother solution for crude crystallization" is a dilute solution prepared by a defecation treatment of the crude DFA III solution with active charcoal or with ion exchange resins or by chromatography or with yeast, if necessary and subjecting the resulting product to solid/liquid separation such as filtration (namely, defecation and filtration). Additionally, the term also means a concentrate of the crude DFA III solution concentrated properly in a concentration apparatus such as efficient can.

(Purified DFA III Solution)

The term "purified DFA III solution" means a solution comprising at least one of a solution prepared by dissolving the crude crystals from crude crystallization in water (lukewarm water) to an appropriate concentration or a fraction of DFA III as obtained by chromatographic separation.

(Mother Solution for Crystallization)

The term "mother solution for crystallization" means a dilute solution prepared by a defecation treatment of the purified DFA III solution with active charcoal or ion exchange resins, or with yeast, if necessary and subsequently subjecting the resulting product to solid/liquid separation such as filtration (namely, defecation and filtration). Additionally, the term also means a concentrate prepared by concentrating at least one of the purified DFA III solution, the crystal syrup, and fractions with DFA III concentrated properly in a concentration apparatus such as effect evaporator.

As described above, the mother solution containing DFA III for crude crystallization and the mother solution containing the same for crystallization are solutions containing DFA III, which are supplied exclusively into crystallizer of cooling mode and/or boiling mode so as to crystallize DFA III.
(Purification and Crystallization Step of DFA III)

The term "purification and crystallization step of DFA III" means a step for defecating and filtering all solutions containing DFA III and subsequently concentrating the filtrates for crystallization, which step ranges from the crude DFA III solutions through crude crystallization to crystallization as a product.
(Solutions Containing DFA III)

The term "solutions containing DFA III" means all solutions containing DFA III as generated in the production flow of the crystals of DFA III, including for example at least one of crude DFA III solutions, mother solutions for the crude crystallization, mother solutions for the crystallization, crude crystal syrup, crystal syrup, purified DFA III solutions, chromatographically separated solutions, and fractions of DFA III as obtained by chromatographic separation (chromatographic fractions of DFA III).

So as to practice the invention, the solutions containing DFA III should be adjusted to pH 5 or more. When the crystallization of DFA III is in progress, the pH decreases to lower the crystal yield, as first found by the inventors. The pH may satisfactorily be 5 or more, preferably 5 to 8, more preferably 6 to 8. A higher pH level is also possible, but the adjustment of the pH requires a larger amount of alkalis such as caustic soda and caustic potassium, uselessly and costly, additionally causing safety problems during labor works.

As to the solutions containing DFA III, at least one and preferably all of those defined above are essentially at pH 5 or more. The pH thereof in a transfer pipe in the production process of the crystals of DFA III including the purification and crystallization step of DFA III is preferably at 5 or more.

As described above, in accordance with the invention, the solutions containing DFA III are essentially at pH 5 or more so as to raise the crystal yield of DFA III. As a consequence of additional research works, unexpectedly, the inventors first found that the presence of sucrose and fructose lowered the crystal yield of DFA III and that the crystal yield of DFA III could be raised when a mother solution for the crystallization contained fructose at 5% or less, preferably 1% or less on a solid content basis. Then, the inventors first verified that such sugar suppression could be attained by adjusting the solution to pH 5 or more. When the solutions containing DFA III are at pH 5 or more and the mother solutions for the crude crystallization and the mother solutions for the crystallization are at a fructose content of 5% or less on a solid content basis and additionally when these conditions are concurrently satisfied, it is found that the maximum crystallization of DFA III can synergistically be raised.
Advantages of the Invention DFA III can be crystallized and produced industrially efficiently when the solutions containing DFA III are at pH 5 or more and fructose content in the mother solutions for the crude crystallization and the mother solutions for the crystallization are at 5% or less on a solid content basis.

The invention is now described in detail in the following Examples but the invention is not limited to these Examples.

EXAMPLE 1

Using a test plant and according to a part of the flow chart shown in FIG. 1, the production of the crystals of DFA III in a recycling mode was tested.

As the levels of sugars in solutions containing DFA III as used at the test, further, the values from the composition analysis by HPLC were used.
(1) Enzymatic Reaction Step An enzyme solution from the culture of *Arthrobacter* sp. strain AHU 1753 (the enzyme titer of about 500,000 U) was added to a solution of 100 kg of commercially available inulin as a daily processable amount (ORAFTI; the product name of RAFTILINE HP), for reaction at 60° C. for 12 hours, to obtain a solution of DFA III prepared enzymatically.
(2) Discoloring and Defecating Step As a discoloring treatment, active charcoal (Futamura Kagaku Kogyo K.K.; Taiko Active Charcoal KW50) was added at a ratio of 0.5% on a solid content basis to the solution of DFA III enzymatically prepared synthetically, for incubation at 80° C. for 30 minutes, followed by filtration through diatomaceous earth.
(3) Crude Crystallization Step The discolored solution of DFA III prepared enzymatically was concentrated to 76% as the solid concentration, which was used as a mother solution for crude crystallization. Then, the seed crystals (seed) were added to the mother solution at 50° C., followed by cooling the resulting mother solution over 12 hours to 10° C. to generate the crude crystals of DFA III. The mother solution of the crude crystals (also referred to as crude crystal massecuite) was centrifuged and separated into the crude crystals and a crude crystal syrup.
(4) Purification and Crystallization Step The crude crystals were again dissolved and then the thus-obtained solution was concentrated to 75% as the solid concentration, which was then used as a mother solution for crystallization. Then, the seed crystals were added to the mother solution at 50° C., and the resulting mother solution was cooled over 12 hours to 10° C. to generate the crystals. The crystal massecuite was centrifuged and separated into the crystals and a crystal syrup.
(5) Recycling Step So as to elevate the recovery ratio of DFA III, 50% of the crude crystal syrup was mixed with the solution after the termination of the enzymatic reaction, while the remaining crude crystal syrup was used as a raw material for feeds. Additionally, 50% of the crystal syrup was back to the evaporator at the crude crystallization step, while the remaining 50% was back to the evaporator at the crystallization step.
(6) Calculation of Crystal Yield The crystal yields of the crude crystals and the crystals were calculated by the following formula in this Example.

$$\text{Crystal yield (\%)} = (P/Q) \times 100$$

In the formula, the individual symbols or alphabets express the following meanings.

P: M–N

Q: (100–N)M/100

M: DFA III purity in mother solution for (crude) crystallization

N: DFA III purity in (crude) crystal syrup.
(7) Production Test

Figure 3:
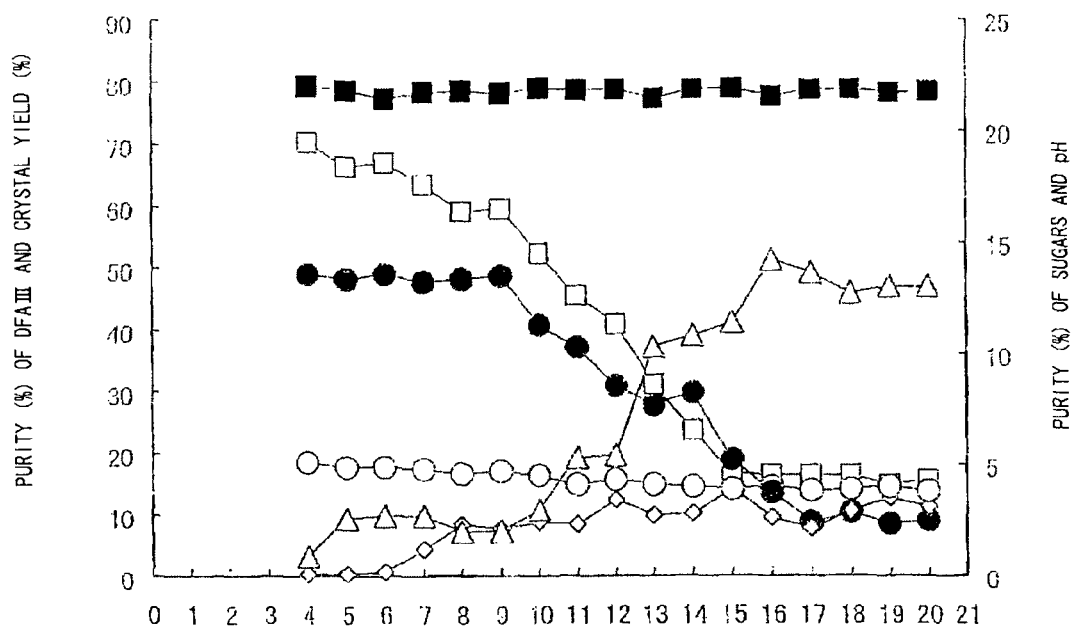
FIG. 3 shows the composition of a mother solution at a step for crude crystallization as well as the crystal yield thereof, where individually, -■- represents the purity of DFA III in dry substance (%); -●- represents the crystal yield (%) of DFA III; -□- represents the purity of fructooligosaccharide in dry substance (%); -◇- represents the purity of sucrose in dry substance (%); -△- represents the purity of fructose in dry substance (%); and -○- represents pH. Hereinbelow, the symbols in FIGS. 4, 5 and 6 represent the same meanings as described above.
Figure 4:
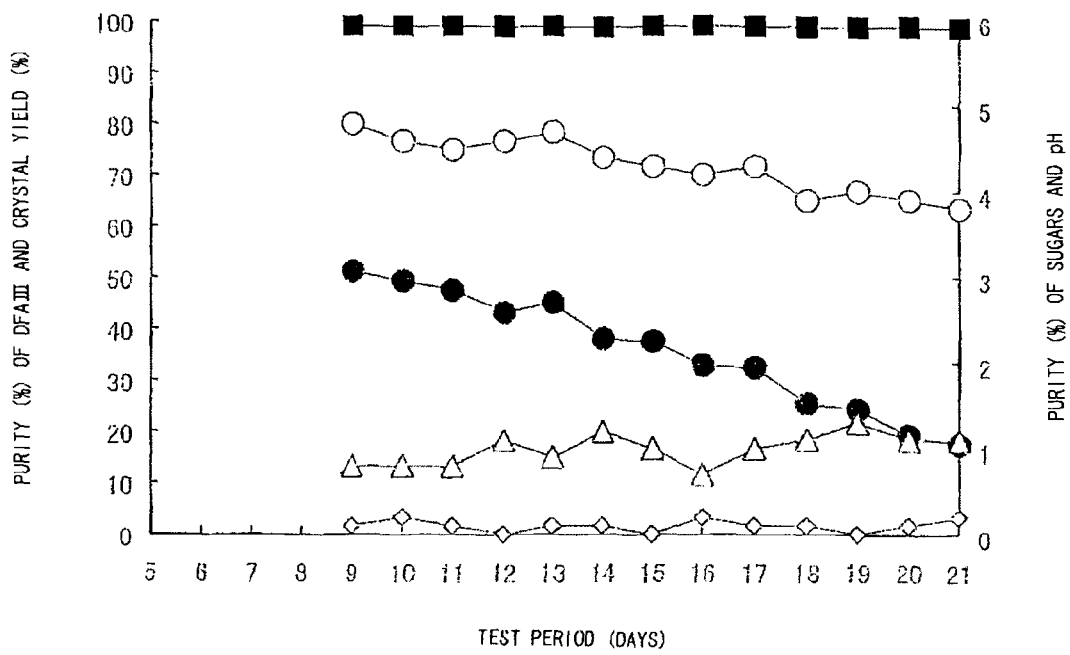
FIG. 4 represents the composition of a mother solution at the step of the crystallization as well as the crystal yield.

According to the steps described above in (1) to (5), production was started. On day 4 from the test start, the step for crude crystallization was initiated, while the step for crystallization was started on day 7 from the test start. The step for crude crystallization is schematically shown (the composition of the mother solution and the crystal yield) in FIG. 3. The crude crystal yield started to decrease on day 10 from test start and decreased to 30% or less on day 13. Therefore, the ratio of the crude crystal syrup to be recycled was reduced from 50% to 30%. Nonetheless, the crystal yield was subsequently lowered continuously. On day 17, the crystal yield was below 10%. The DFA III purity in the mother solution for crude crystallization was a little less than 80% throughout the test period, with no larger variation. Concerning the composition of impurities, meanwhile, fructooligosaccharide was decreased over time during the test, while fructose believed as a decomposition product thereof was increased. The mother solution for crude crystallization was at pH 5.1 at the test start and was gradually decreased to around 4. The purification and crystallization step is schematically shown in FIG. 4. No large variation in the sugar composition during the period was observed, while the crystal yield was gradually lowered during the test period. The mother solution for crystallization was at pH 4.8 at the start and was gradually decreased to around 4.

EXAMPLE 2

Example 1 apparently indicated that the crystal yield of DFA III was gradually lowered when DFA III was produced in the recycling mode. Because the mother solution of crystallization was at a decreased pH, which was accompanied by the progress of the decomposition of fructooligosaccharide, then, some relation between the decrease of the crystal yield and the decomposition progress was suggested. At the production test in this Example, caustic soda was added to the mother solution for crude crystallization (the solution before concentration) and a solution of the crude crystals redissolved, after the termination of the enzymatic reaction, to prevent the pH decrease of the solutions at the individual steps. Except for the procedure, the production was done by the same method as in Example 1.

Figure 5:
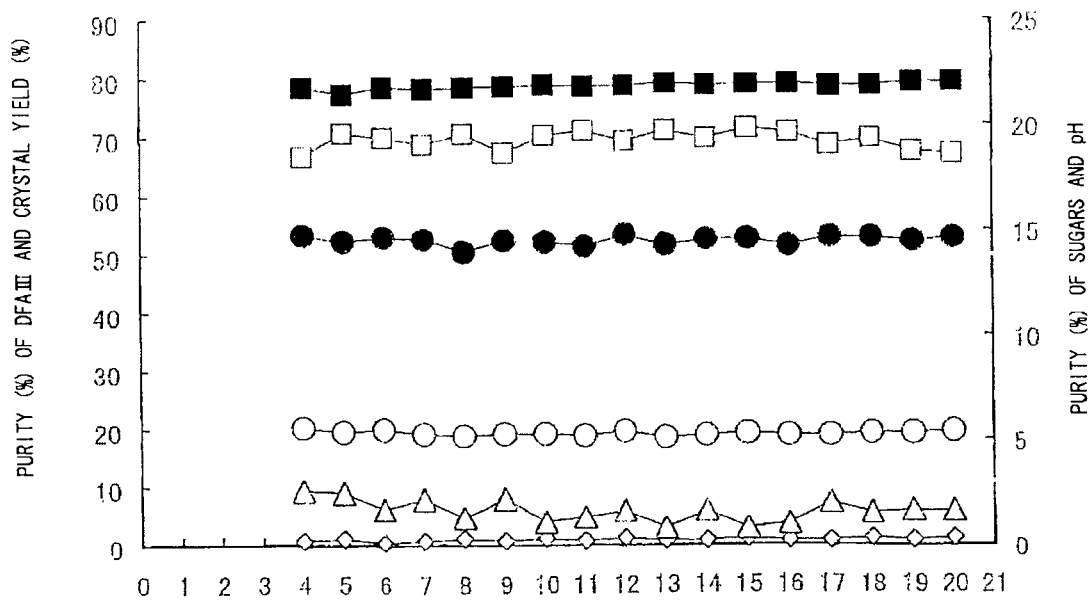
FIG. 5 represents the composition of a mother solution at the step of the crude crystallization as well as the crystal yield, when the pH during the purification and crystallization step was maintained at 5 or more via the addition of caustic soda.
Figure 6:
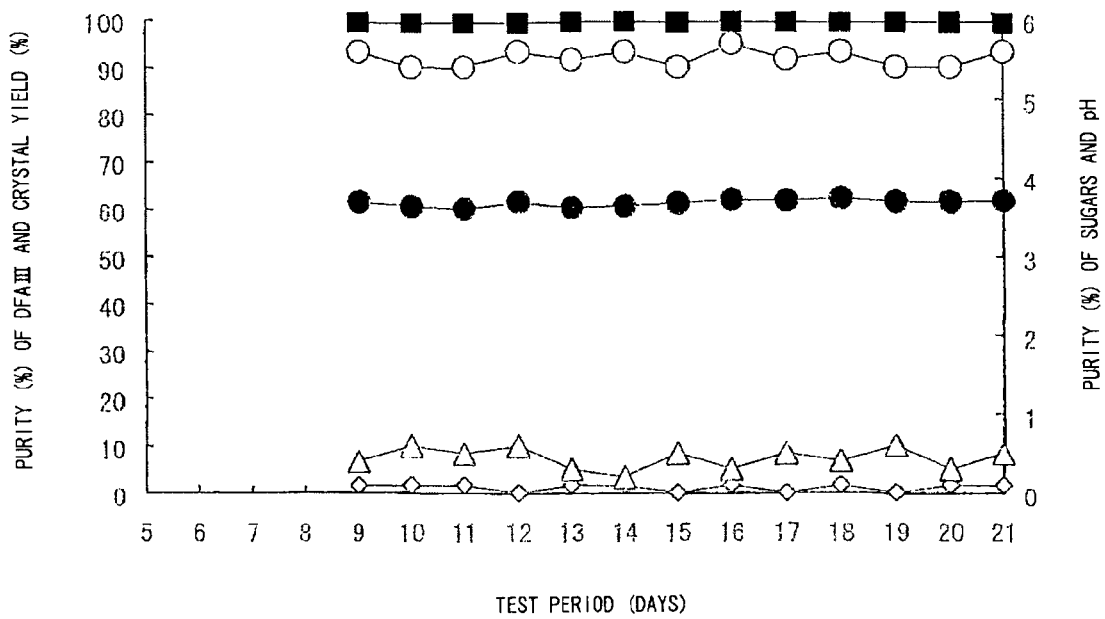
FIG. 6 represents the composition of a mother solution at the step of the crystallization as well as the crystal yield, when the pH during the purification and crystallization step was maintained at 5 or more via the addition of caustic soda.

The step for crude crystallization and the step for crystallization are schematically shown in FIGS. 5 and 6. Via the addition of caustic soda, the individual mother solutions for such crystallization changed within a range of 5.1 to 5.6 and a range of 5.4 to 5.7, respectively, while the decomposition of fructooligosaccharide was suppressed. Additionally, the individual crystal yields could be retained at high levels.

EXAMPLE 3

Compared with other sugars, DFA III itself is a substance highly resistant against heat and acids. When the solutions at the production steps are at lower pHs in the industrial steps for producing DFA III as shown in FIG. 1, impurities are decomposed to generate other substances except DFA III. Additionally because solutions containing DFA III for use in the crystallization are recycled and used, it is indicated that the pH thereof is increasingly reduced while other substances except DFA III also accumulate. In the test production in Example 1, actually, the pH of the solutions at the steps is gradually decreased, causing the decrease of the ratio of fructooligosaccharide, so that fructose accumulates.

The inventors therefore carried out a table test so as to determine how the sugar composition of the solution after the termination of the enzymatic reaction as prepared in Example 1 was modified under conditions of pH (3 to 7) and temperature (70° C., 80° C.) Consequently, almost no modification of the composition of the contained sugars was observed in 24 hours under conditions of 70° C. and pH 5 or more. At pH 4, the decomposition of sugars such as tetrasaccharides and larger saccharides and the increase of fructose were observed in 8 hours. At pH 3, the tendency was further enhanced. The modification of the sugar composition as observed under individual pH conditions at 70° C. was further accelerated when the temperature was at 80° C. At 80° C., almost no modification thereof was observed in 12 hours even at pH of 5 or more, in the same manner as observed at 70° C. At the time 24 hours later, however, the decomposition of sugars such as tetrasaccharides and larger saccharides and the increase of fructose were likely observed.

The inventors further examined acidic substances in the mother solution for the crude crystallization in Example 1, which was at a decreased pH of 4. It was found that the mother solution contained organic acids (lactic acid, acetic acid, formic acid, etc.) at a concentration of 30 to 40 mg/100 g•sample. At a table test, the inventors found that in the resulting aqueous fructose solution when left to stand alone in environment at 80° C. for a long time, organic acids increased gradually, involving the decrease of the pH.

Based on the results of the analytical values in Examples 1 through 3, the inventors carried out table tests in Examples 4 through 7, so as to find how highly variable fructooligosaccharide, organic acid, fructose, sucrose and pH affected the crystal yield. Herein, the crystal yield was calculated according to the following formula, which was used in Examples 4 to 7.

$$\text{Crystal yield (\%)} = A/B \times 100$$

In the formula, the individual symbols and alphabets represent those described below.

A: the weight (in gram) of the crystals of DFA III obtained via crystallization

B: the content (in gram) of DFA III in a mother solution for crystallization

EXAMPLE 4

Crystal Yield when a Sucrose Solution or a Fructose Solution was Added to an Aqueous Solution of DFA III at a Purity of 99.9%)

Figure 7:
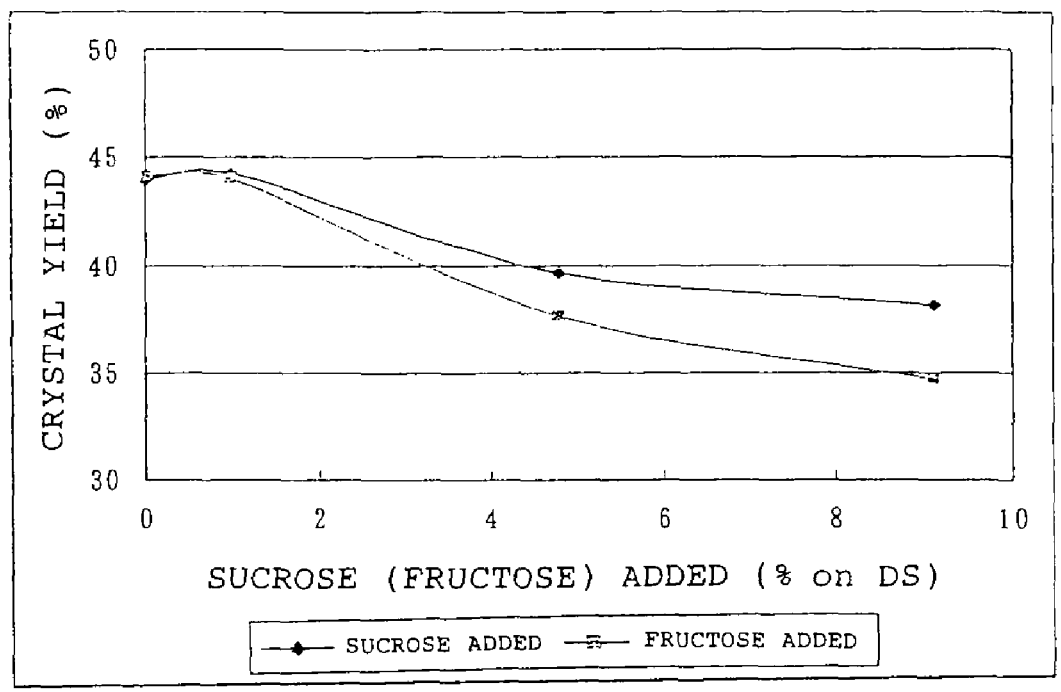
FIG. 7 shows the change of the DFA III crystal yield in case that sucrose- and fructose solutions were added to the DFA III solution.

A sucrose solution at a solid concentration of 71% or a fructose solution at a solid concentration of 71% was added at 3 g, 15 g, and 30 g (1.0, 4.8 and 9.1%, respectively as the amount of sucrose (fructose) on a solid content basis) to 300 g of a DFA III solution adjusted to a solid concentration of 71%, for crystallization. A control with no addition of such sucrose solution or fructose solution was also used for crystallization. At a test where the sucrose (fructose) solution was added at 30 g, the seed crystals were dissolved thoroughly during seeding at 50° C. Therefore, seeding was again done at 45° C. Then, the solutions were cooled to 10° C. to grow the crystals. The test results are shown in FIG. 7. By using mother solutions for crystallization at a constant solid concentration and at a constant DFA III amount while increasing the amounts of sucrose and fructose to be added, the amount of the crystals generated was measured. Following the increase of the amounts added, the amount of the crystals of DFA III generated was decreased in both cases.

EXAMPLE 5

Influence of Impurities Contaminated in DFA III-Containing Solution on Crystal Generation (1) A test was done by using mother solutions at a constant solid concentration and a constant DFA III amount. Consequently, the amount of the generated crystals of DFA III was decreased, following the increase of the amounts of sucrose and fructose added. Because it was suggested that the results might potentially be ascribed to the reduction of the purity of DFA III, the influence of the difference in contaminated impurities on the crystal generation was tested.

A fructooligosaccharide (MEIOLIGO P manufactured by Meiji Seika Kaisha, Ltd.: a mixture of tetrasaccharides, trisaccharides, disaccharides, and fructose at the contents of 65.2%, 32.8%, 1.2%, and 0.8%, respectively on a solid content basis) solution at a solid concentration of 71%, a sucrose solution and a fructose solution both at a solid concentration of 71% were individually added at 30 g (9.1% on a solid content basis) to 300 g of a DFA III solution adjusted to a solid concentration of 71%, for crystallization. A control with no addition of such solutions was also used for crystallization. The seeding temperature was 45° C. The solutions were cooled to 10° C. to grow the crystals. The test results are shown in FIG. 8.

Figure 8:
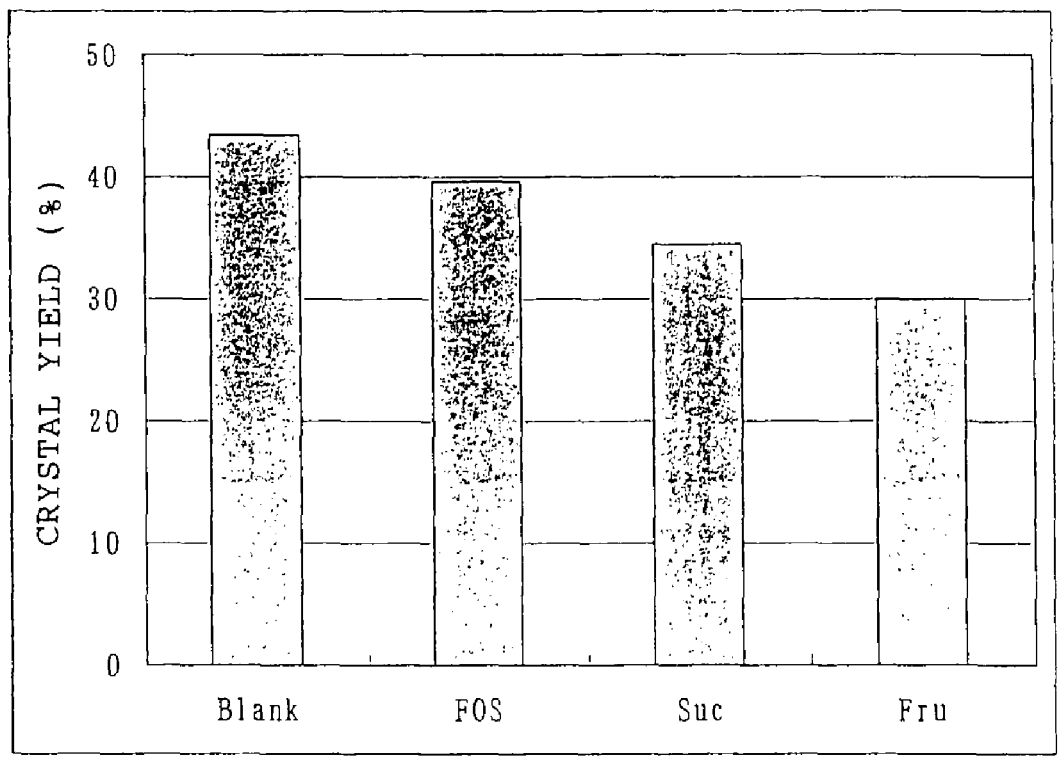
FIG. 8 shows the influence (1) of fructooligosaccharide, sucrose and fructose contained in a DFA III-containing solution on the DFA III crystal yield. In the figure, individually, FOS represents fructooligosaccharide; Suc represents sucrose; Fru represents fructose; Blank represents control.

FIG. 8 shows the results that in the case of replacing fructooligosaccharide with sucrose or fructose compared with the presence of fructooligosaccharide alone as impurities, the amount of the crystals of DFA III generated was less and that the crystallization of DFA III was suppressed even at the same DFA III purity when fructooligosaccharide was decomposed to generate sucrose and fructose. Such results were verified.

(2) Influence of Composition of Impurities Contaminated in DFA III on Crystal Generation Then, the influence of the presence of sucrose or fructose alone or the presence of both sucrose and fructose was examined.

A sucrose solution at a solid concentration of 71%, and a fructose solution at a solid concentration of 71%, were individually added at 30 g (9.1% on a solid content basis) to 300 g of a DFA III solution adjusted to a solid concentration of 71%, for crystallization. A combination of the sucrose solution at 15 g and the fructose solution at 15 g was also added to 300 g of the DFA III solution (the total of sucrose and fructose corresponds to 9.1% on a solid content basis). A control with no addition of such sucrose solution or fructose solution or the combination was also used for crystallization. The seeding temperature was 45° C. The solutions were cooled to 10° C. to grow the crystals. The test results are shown in FIG. 9.

Figure 9:
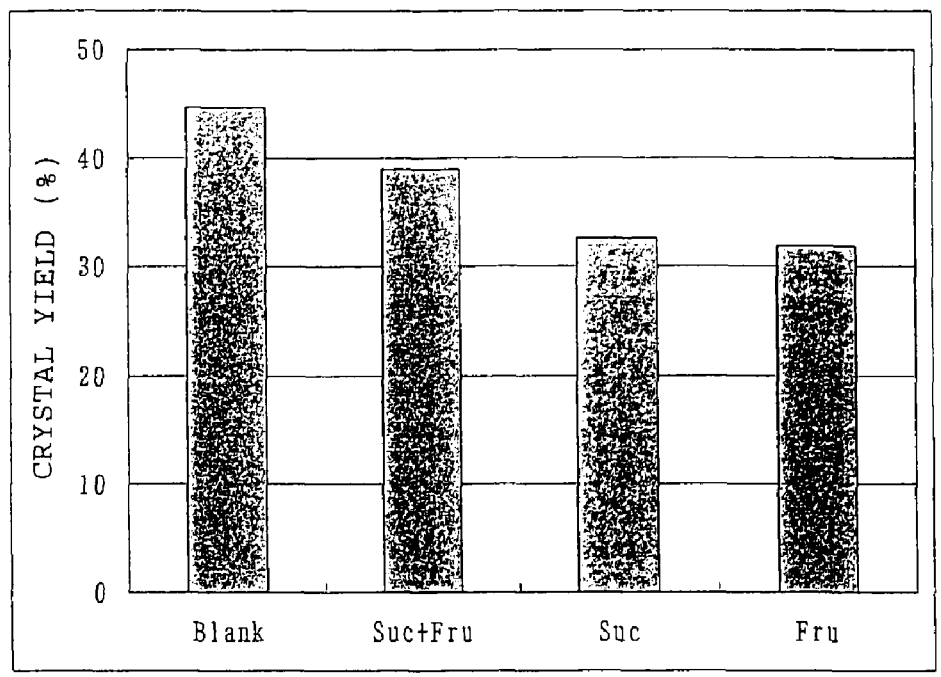
FIG. 9 shows the influence (2) of the contents of sucrose (Suc), fructose (Fru), and sucrose in combination with fructose (Suc+Fru) in a DFA III-containing solution on the DFA III crystal yield.

FIG. 9 shows the results that the single addition of sucrose or fructose was more highly inhibitory than the addition of sucrose and fructose individually at half of their amounts described above, even at the same purity of DFA III. Therefore, it was suggested that the DFA III crystallization might be influenced by a higher content of either sucrose or fructose existing as impurities. However, the amount of sucrose generated never exceeds the amount of fructose generated, on site in producing the crystals. Hence, it is indicated that the amount of the crystals generated may be influenced by the amount of fructose.

Compared with the presence of fructooligosaccharide alone as impurities, it was indicated that the presence of sucrose and fructose generated a smaller amount of the crystals of DFA III, where the level of the generation was influenced by either one of sucrose and fructose, which is at a higher content. At the same level of impurities, nonetheless, the amount of the crystal generated was larger than in the control, when sucrose crystals or fructose crystals in solids were added to the DFA III solution. Thus, it was indicated that the DFA III crystals could be recovered even in the presence of sucrose and fructose, at a yield similar to the case in the absence of both sucrose and fructose, by raising appropriately the concentration of the mother solution.

(3) Influence of the Composition of Impurities Contaminated in DFA III Solution on Crystal Generation Then, it was examined the influence of organic acids of which the presence was confirmed by the analysis of the solutions at the steps. The organic acids of which the presence was confirmed in the solutions at the steps were lactic acid, acetic acid, formic acid and other acids (with plural peaks unidentified). Herein, acetic acid and formic acid generated during the thermal decomposition of fructose were tested. Because the analytical results of the solutions at the steps indicate that the contents of the individual organic acids detected in the concentrate solution from the defecated and filtered solution of the crude DFA III solution were about 30 to 40 mg/100 g•sample, the amounts of individual salts of the organic acids to be added were adjusted to 0 to 100 mg/100 g•DFA III solution.

A mix solution of sodium acetate and sodium formate was added to give respective contents of 10 mg of sodium acetate and 10 mg of sodium formate, 50 mg of sodium acetate and 50 mg of sodium formate, and 100 mg of sodium acetate and 100 mg of sodium formate per 100 g•DFA III solution, to 300 g of the DFA III solution adjusted to a solid concentration of 71%, to which pure water was added so as to adjust the solid concentration (to the final solid concentration of 70.3%), for crystallization. A control with no addition of any such mix solution was also adjusted to the same solid concentration, by adding pure water. The seeding temperature was 50° C. The solutions were cooled to 10° C. to grow the crystals. The test results are shown in FIG. 10.

Figure 10:
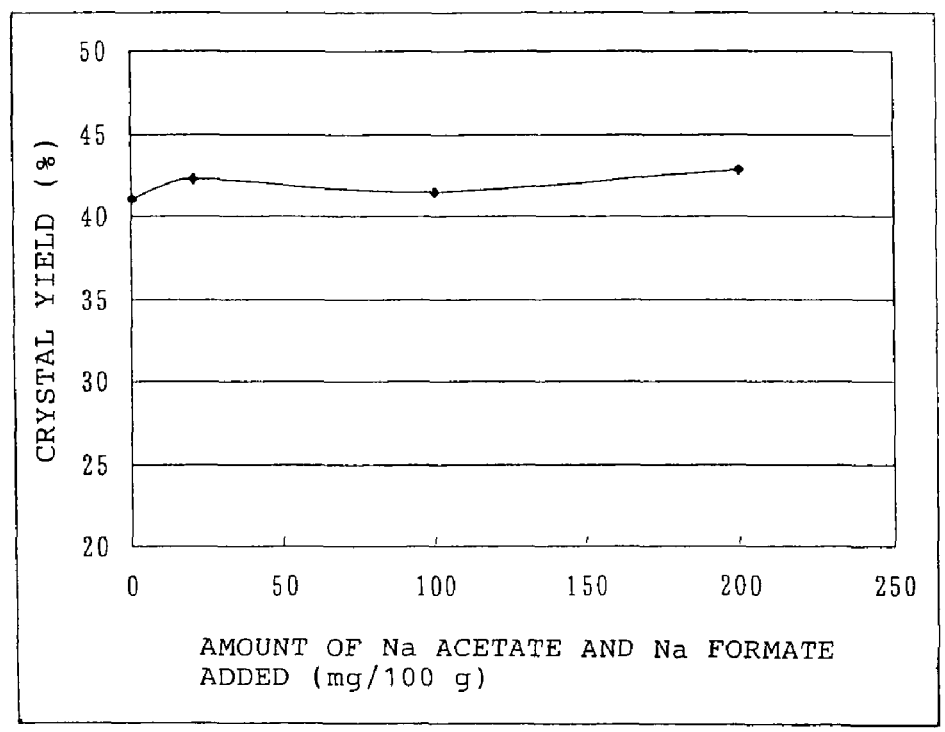
FIG. 10 shows the influence of organic acid salts (Na acetate+Na formate) contained in a DFA III-containing solution on the DFA III crystal yield.

FIG. 10 indicates that the organic acid salts never inhibited the crystallization of DFA III despite some variation of the amount of the crystals generated. Further, the crystal generation in the control and in the DFA III solution, to which sodium acetate and sodium formate were individually added at 10 mg/100 g, proceeded slowly, immediately after the seeding, because these solutions were at lower solid concentration, namely 70.3% which was slightly lower concentration than the conditions of the past tests. Compared with these results, the crystal generation in the DFA III solutions to which sodium acetate and sodium formate were individually added at 50 mg/100 g and at 100 mg/100 g proceeded faster, immediately after the seeding. It was examined what caused the discrepancy. It was indicated that since the mix solution of sodium acetate and sodium formate was at such a high pH of 8.6, the mother solution after the mixture solution was added was around pH 7 in the latter case. Therefore, the inventors considered that the change of the pH of the solutions at the steps due to the generation of organic acids at the production steps might have some influence on the generation of the crystals of DFA III.

EXAMPLE 6

Influence of pH on the DFA III crystallization (1) So as to verify the influence of the pH of the mother solution for use in crystallization on the generation of the crystals of DFA III, the change of the generated crystal amount was examined at variable pHs in the presence of organic acid salts (sodium acetate and sodium formate).

A solution of sodium acetate and sodium formate was added at 100 mg sodium acetate and 100 mg sodium formate per 100 g•DFA III solution to 300 g of the DFA III solution adjusted to a solid concentration of 73%. The resulting solution was adjusted to pH 7, 5, 4 and 3, with 5N hydrochloric acid, and adjusted to a solid concentration of 71% with pure water, for crystallization. The seeding temperature was 50° C. The solution were cooled to 25° C. to grow the crystals. The test results are shown in FIG. 11.

Figure 11:
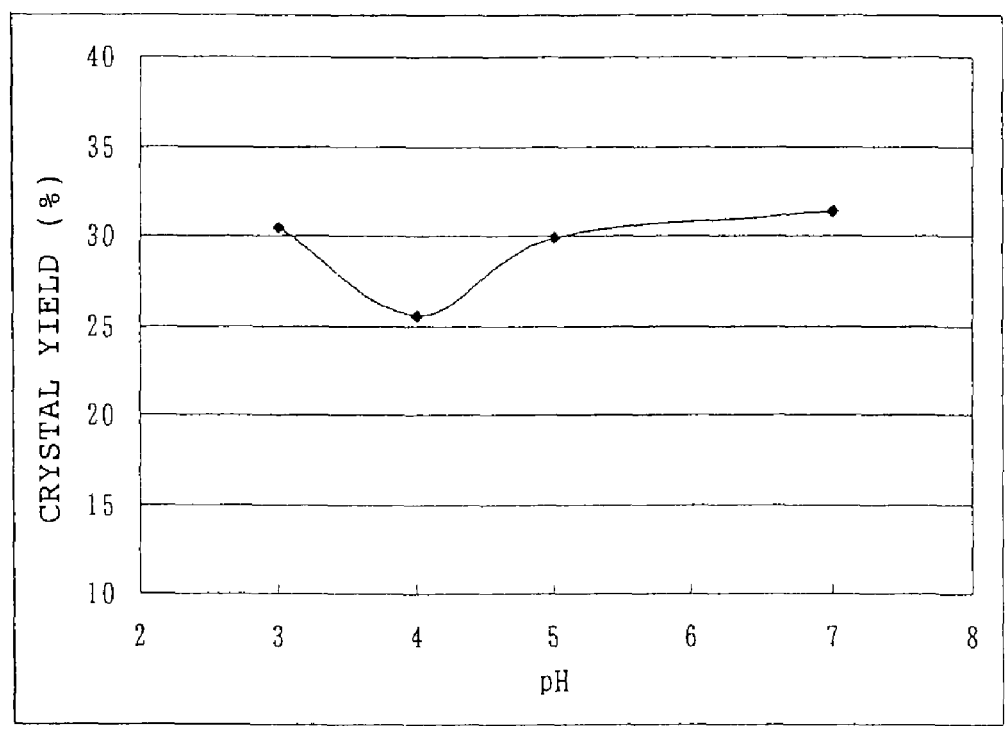
FIG. 11 shows the influence (1) of the pH of a DFA III-containing solution on the DFA III crystal yield.

FIG. 11 shows the results that the amount of the crystals generated was influenced by the pH and that the amount thereof was the largest at the pH 7, was the smallest at the pH 4, and was the same level at pH 3 and the amount at pH 5.

Figure 12:
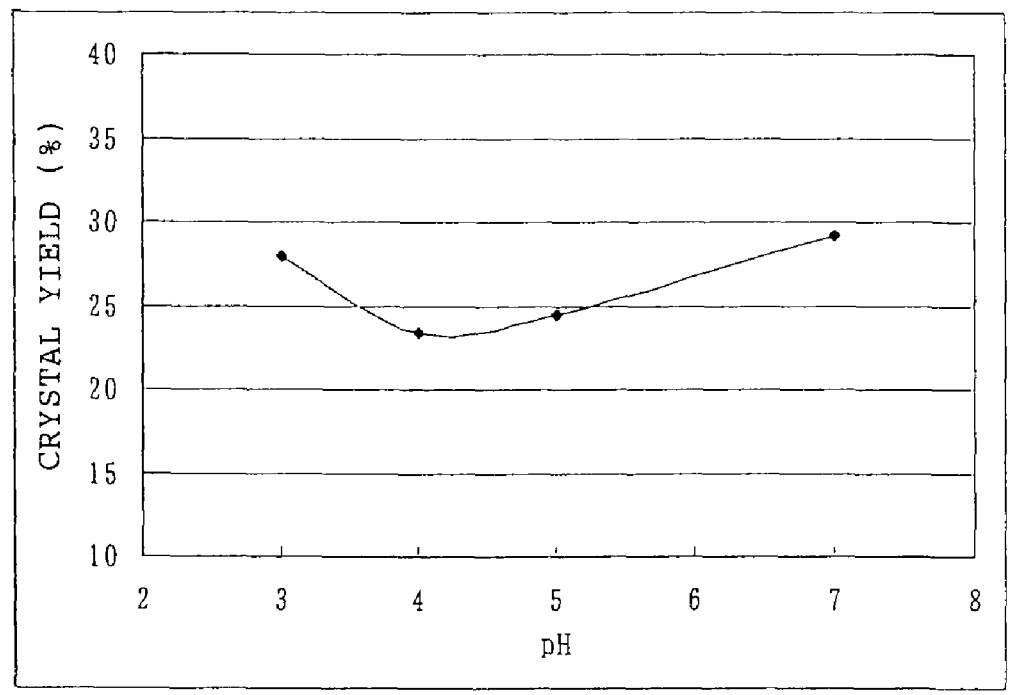
FIG. 12 shows the influence (2) of the pH of a DFA III-containing solution on the DFA III crystal yield.

(2) So as to examine whether or not the phenomenon depended singly on pH and occurred even without any presence of organic acid salts, the DFA III solution was pH 5 adjusted with hydrochloric acid and caustic soda, to test the change of the amount of the crystals generated. 300 g of the DFA III solution adjusted to a solid concentration of 71.5% was adjusted to pH 7, 5, 4 and 3 with 1N hydrochloric acid and 1N caustic soda, to which pure water was subsequently added to adjust the solid concentration of 71%, for crystallization. The seeding temperature was 50° C. The solutions were cooled to 25° C. to grow the crystals. The test results are shown in FIG. 12.

The test results are more or less different from the results in the presence of organic acid salts, in that the amount of the crystals generated at pH 5 was less. However, the same results were obtained in that at pH 7, the amount of the crystals generated was the largest, with the amount was at minimum at pH 4. So as to verify that the results were never attributed to the difference in the concentration of inorganic acids, further, the pH adjustment was done in the same manner in the presence of 1% sodium chloride, for crystallization. The results were similar to those when the crystallization was done after the pH adjustment in the presence of organic acid salts. This indicates that the presence of salts reduces the crystallization inhibitory action at pH 5.

(3) Those described below were verified using the crude crystal mother solution at a practical step.

Figure 13:
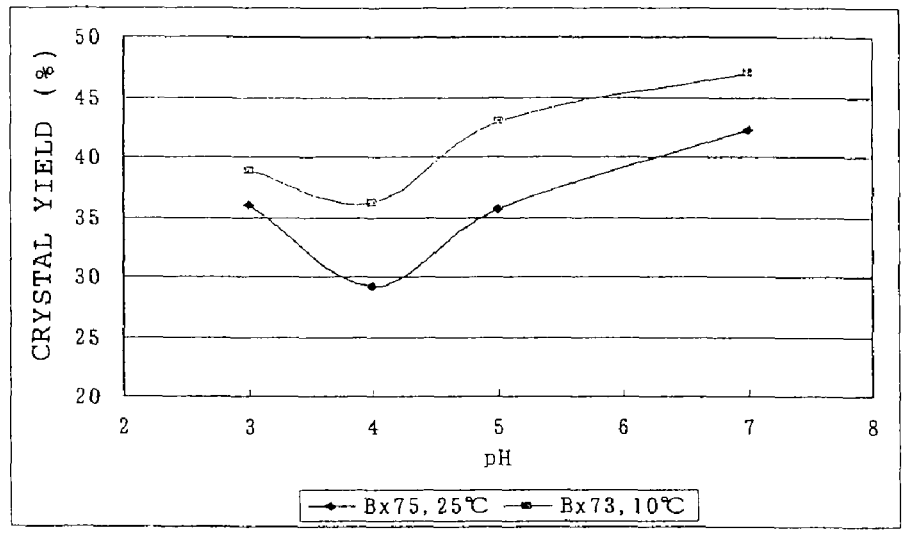
FIG. 13 shows the influence (1) of the pH of a mother solution for the crude crystallization on the DFA III crystal yield.

After the crystals deposited in a crude crystal mother solution collected (at a DFA III purity of 75.9%) were completely dissolved, the resulting solution was concentrated to about 76% as a solid concentration, which was adjusted to pH 7, 5, 4 and 3 with 5N hydrochloric acid or 5N caustic soda. Pure water was added to adjust the solid concentration to 75 (or 73) %, for crystallization. The solution were cooled to 25° C. to grow the crystals, which were at a solid concentration of 75%, while the solutions were cooled to 10° C., which were at a solid concentration of 73%. The seeding temperature was 50° C. (at a solid concentration of 75%) or 45° C. (at a solid concentration of 73%). The test results are shown in FIG. 13. At any of the solid concentrations, the crystal yield of DFA III was the smallest at pH 4.

EXAMPLE 7

Influence of the pH of the Mother Solution for (Crude) Crystallization and Supersaturation Degree on DFA III So as to determine the optimal concentration level of the mother solution for crystallizing DFA III vs. the pH change as a factor inhibiting the DFA III crystallization, examination was done.

Figure 14:
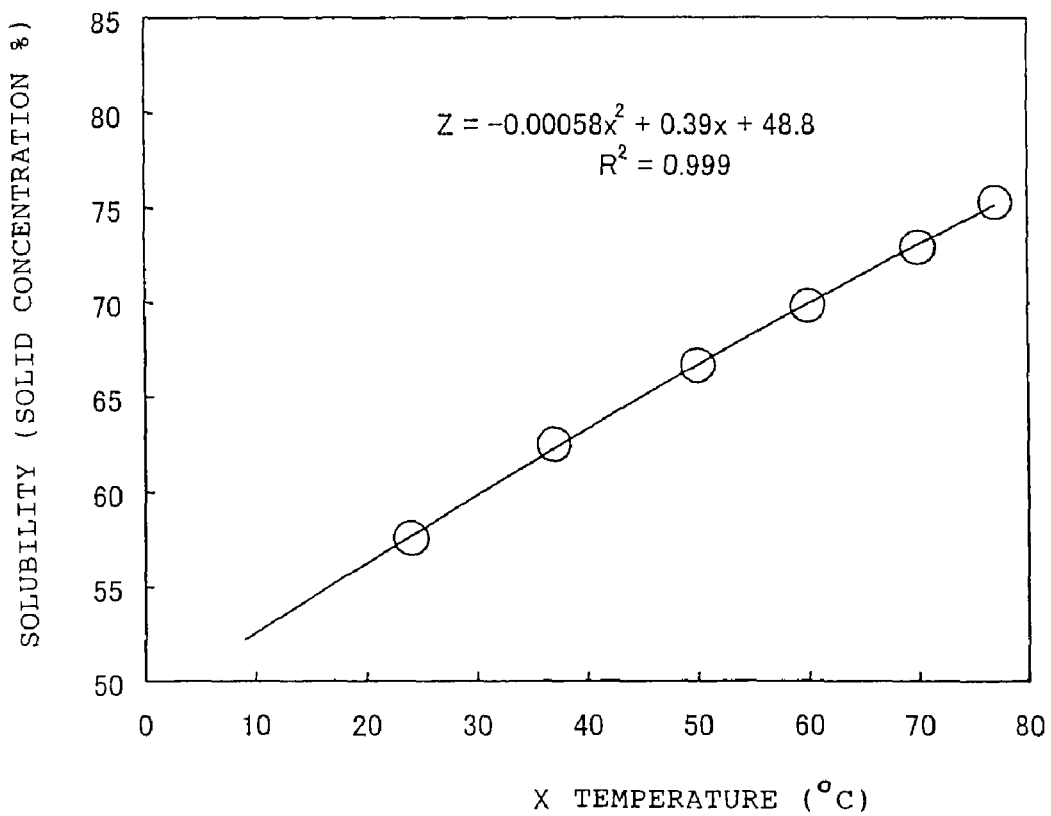
FIG. 14 shows the solubility of DFA III and an approximate curve of the solubility. In the figure, the symbol "○" expresses the solubility of DFA III (observed value) while the symbol "–" expresses an approximate curve of the DFA III solubility.

As shown in FIG. 14, beforehand, the solubility of DFA III (saturated solid concentration %) at respective temperature was examined. Based on the measured levels, an approximate curve of the solubility was first formulated and calculated as represented by the following formula (correlation coefficient $R^2$=0.999).

Solubility (saturated solid concentration %)"$Z$"= $-0.00058X^2 + 0.39X + 48.8$

Herein, X represents temperature (° C.).

Then, the supersaturation degree "S" of the mother solution for the DFA III crystallization at a purity "P" to the DFA III solubility at the temperature "X"° C. on completion of cooling crystallization was defined by the following formula. The supersaturation degree "S" was the concentration level required for the crystallization of the mother solution for the DFA III crystallization, as expressed in numerical figure.

Supersaturation degree"$S$"=$[Y \times P/(100-Y)]/[Z/(100-Z) \times 100]$

Herein, Y: the solid concentration of the mother solution for the DFA III crystallization (%);
P: the purity of DFA III in the mother solution for the DFA III crystallization (%); and
Z: solubility (X: the temperature on completion of cooling crystallization (° C.)).

Using subsequently the DFA III solutions at practical steps, the influence of the supersaturation degree "S" defined above on the DFA III crystallization was examined at a table test under variable pHs of the mother solutions for crystallization, as factors inhibiting the crystallization. The pH adjustment was done by adding 5N HCl or 5N NaOH to the DFA III solutions from the steps. After the solutions were concentrated to various concentrations, the resulting individual solutions were used as mother solutions for the crystallization, for seeding at 50° C. and cooling down to 10° C. for growing the crystals. According to the formula, the supersaturation degree "S" was calculated at the temperature 10° C. on the completion of cooling crystallization.

The results about the examination of the relation between the pH of the mother solutions for the crystallization and the supersaturation degree "S" are shown in Table 1. When the mother solutions for the crystallization were at pH 5 to 7, the massecuite flowability was significantly reduced in the mother solutions containing DFA III at any purity for the crystallization, under conditions that the supersaturation degree "S" was 4.4 or more. Thus, apparently, purging was tough. Under conditions that the supersaturation degree "S" was 4.1 or less, meanwhile, the massecuite was at such appropriate flowability that the purging could be done without any difficulty. It was indicated that the supersaturation degree "S" on the basis of the temperature on the completion of the crystallization was 4.1 or less under industrial conditions for producing the crystals of DFA III where the mother solutions for the crystallization were at pH 5 or more. When the supersaturation degree "S" was less than 1.3, the crystal yield was 20% or less. From the standpoint of the crystal yield, it was indicated that the supersaturation degree "S" was preferably 1.3 or more to 4.1 or less, more preferably 1.5 or more to 4.1 or less, still more preferably 2.3 or more to 4.1 or less.

TABLE 1

Influences of the pHs of the various DFA III-containing solutions and the supersaturation degree "S" on the crystal yield

| Supersaturation | pH of mother solution for crystallization | | |
|---|---|---|---|
| degree "S" | 5 | 6 | 7 |
| Crystal yield (%) of DFA III-containing solution "A" by cooling crystallization | | | |
| 1.3 | 21.0 | 21.6 | 21.9 |
| 1.5 | 29.4 | 31.0 | 31.4 |
| 1.6 | 36.0 | 36.8 | 37.0 |
| 2.3 | 53.1 | 55.3 | 56.1 |
| 4.1 | 67.1 | 68.5 | 68.8 |
| 4.7 | x | x | x |
| Crystal yield (%) of DFA III-containing solution "B" by cooling crystallization | | | |
| 1.3 | 20.6 | 21.1 | 21.3 |

TABLE 1-continued

Influences of the pHs of the various DFA III-containing solutions and the supersaturation degree "S" on the crystal yield

| Supersaturation degree "S" | pH of mother solution for crystallization | | |
|---|---|---|---|
| | 5 | 6 | 7 |
| 1.5 | 31.2 | 32.4 | 32.6 |
| 1.6 | 36.1 | 36.8 | 38.1 |
| 2.3 | 53.3 | 54.2 | 54.7 |
| 4.1 | 65.0 | 65.1 | 65.4 |
| 4.7 | x | x | x |

Composition of solid contents in the solution "A": DFA III at 99.5%, ashes at 0.1%, fructooligosaccharide at 0.4%, Composition of solid contents in the solution "B": DFA III at 79.7%, ashes at 0.3%, fructooligosaccharide at 18.3%, sucrose at 0.2% and fructose at 1.0%.

In the table, the symbol "x" represents that purging was tough due to the decrease of the massecuite flowability.

Accession No.: FERM BP-8296

Bacterial strain deposited: *Arthrobacter* sp. AHU 1753

Name of Depositary: The International Patent Organism Depositary, The National Institute of Advanced Industrial Science and Technology (AIST)

Address of Depositary: AIST Tsukuba Central 6, 1-1, Higashi 1-chome, Tsukuba-shi, Ibaraki-ken, 305-8566, Japan (zip code: 305-8566)

Deposition Date: Feb. 18, 2003

The invention claimed is:

1. A process for producing crystals of difructose dianhydride III (DFA III), comprising:
   defecating and filtering a solution containing DFA III to obtain a filtrate; and
   concentrating the filtrate to induce crystallization of the DFA III,
   wherein the solution and the filtrate are maintained at a pH of 5 or higher.

2. The process of claim 1, wherein the solution containing DFA III is a solution prepared by reacting inulin with fructosyltransferase in a solution and defecating and filtering the solution.

3. The process of claim 2, wherein the inulin has fructose polymerization degree of 10 to 60 and has a polysaccharide purity of 70% or more in a dry state.

4. The process of claim 1, wherein (1) the fructose content of the filtrate is 5% or less on a solid content weight basis and (2) the supersaturation degree of filtrate is 1.3 to 4.1.

5. The process of claim 2, wherein (1) the fructose content of the filtrate is 5% or less on a solid content weight basis and (2) the supersaturation degree of the filtrate is 1.3 to 4.1.

6. The process of claim 4, further comprising adjusting the fructose content to 5% or less on a solid content weight basis by removing fructooligosaccharide and/or fructose by chromatography method and/or yeast treatment.

7. The process of claim 5, further comprising adjusting the fructose content to 5% or less on a solid content weight basis by removing fructooligosaccharide and/or fructose by chromatography method and/or yeast treatment.

8. The process of claim 1, wherein the solution and the filtrate are maintained at a pH of 5 to 8.

9. The process of claim 1, wherein the solution and the filtrate are maintained at a pH of 6 to 8.

10. The process of claim 1, wherein the concentrated filtrate has a solid content of 60 to 85%.

11. The process of claim 1, wherein the DFA III crystals have a melting point of 163.7° C. and an optical rotation of 134.5°.

12. The process of claim 1, further comprising separating the crystals of DFA III from a crystal syrup and recycling the crystal syrup to the defecating and filtering step.

13. The process of claim 1, which also comprises a recycling system for recycling the crude crystal syrup to the crystallization step to continuously produce the crystals of DFA III.

* * * * *